United States Patent [19]

Schmidt et al.

[11] 4,307,898

[45] Dec. 29, 1981

[54] CARBONLESS DUPLICATING AND MARKING SYSTEMS

[75] Inventors: Paul J. Schmidt, Sharonville; William M. Hung, Cincinnati, both of Ohio

[73] Assignee: Sterling Drug Inc., New York, N.Y.

[21] Appl. No.: 127,648

[22] Filed: Mar. 6, 1980

[51] Int. Cl.$^3$ .................... B41M 5/16; B41M 5/18; B41M 5/22

[52] U.S. Cl. ................... 282/27.5; 427/151; 428/488; 428/537; 428/913; 428/914; 428/320.4; 430/348; 430/964

[58] Field of Search ............ 260/319.1, 326.12 R, 260/326.15, 326.16; 282/27.5; 427/151; 428/307, 411, 537, 913, 914, 488; 430/200, 348, 964

[56] References Cited

U.S. PATENT DOCUMENTS

| | | | |
|---|---|---|---|
| 3,637,748 | 1/1972 | Psaar et al. | 260/326.15 |
| 3,684,510 | 8/1972 | Psaar et al. | 96/48 R |
| 3,957,288 | 5/1976 | Lemahieu | 282/27.5 |
| 3,958,815 | 5/1976 | Poot et al. | 282/27.5 |

*Primary Examiner*—Bruce H. Hess
*Attorney, Agent, or Firm*—Paul E. Dupont; B. Woodrow Wyatt

[57] ABSTRACT

3-[(Alkoxy)(aryl or heteroaryl)methyl]-1H-indoles which are useful as color formers in pressure-sensitive carbonless duplicating systems and thermal marking systems are prepared by reacting 3-[(arylsulfonyl)(aryl or heteroaryl)methyl]-1H-indoles with alcohols in the presence of a base.

5 Claims, No Drawings

CARBONLESS DUPLICATING AND MARKING SYSTEMS

BACKGROUND OF THE INVENTION

1. Field of the Invention

The present invention relates to a group of compounds classified in the field of organic chemistry as 3-[(alkoxy)(aryl or heteroaryl)methyl]-1H-indoles which are useful as colorformers in pressure-sensitive carbonless duplicating systems and thermal marking systems; to processes for the preparation thereof and to pressure-sensitive carbonless duplicating systems and thermal marking systems containing the same.

2. Description of the Prior Art

Several classes of organic compounds of widely diverse structural types are known to be useful as color formers for carbonless duplicating systems. Among the most widely recognized classes are the phenothiazines, for example, benzoyl leuco methylene blue; fluorans, for example, 2'-anilino-6'-diethylaminofluoran; phthalides, for example, crystal violet lactone; methine dyes, for example, Michler's hydrol and derivatives thereof and various other types of color formers currently employed in commercially accepted carbonless duplicating systems. Typical of the many such systems taught in the prior art are those described in U.S. Pat. Nos. 2,712,507, 2,800,457 and 3,041,289 which issued July 5, 1955, July 23, 1957 and June 26, 1962, respectively. Many of the color formers in the prior art suffer one or more disadvantages such as low tinctorial strength poor light stability, poor xerographic copiability, low resistance to sublimation, and low solubility in common organic solvents, the latter disadvantage thus requiring the use of specialized and expensive solvents in order to obtain microencapsulated solutions of sufficient concentration for use in pressure-sensitive copying systems.

The following appear to constitute the most relevant prior art relative to the present invention.

U.S. Pat. No. 3,684,510, patented Aug. 15, 1972 discloses indolylmethane derivatives having the formula

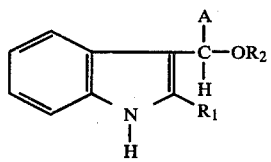

in which A is aryl or a heterocyclic aromatic group and $R_1$ and $R_2$ are hydrogen, alkyl or aralkyl. The compounds are stated to be useful in combination with arylamino compounds and tetrahalomethane compounds in light-sensitive materials for the production of copies from an original.

U.S. Pat. No. 3,958,815 issued May 25, 1976 discloses in most pertinent part a group of compounds stated to be useful as dye precursors in pressure-sensitive recording materials and having the formula

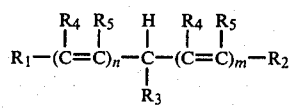

wherein inter alia $R_1$ and $R_2$ represent (1) an aryl group substituted with an ether group $R_6$—O— in which $R_6$ represents a hydrocarbon group or (2) a heterocyclic group; $R_3$ represents a —XH or —X—$R_7$ group in which X is oxygen or sulfur and $R_7$ is an organic group, and m and n are 0.

French Pat. No. 1,561,663 published Mar. 28, 1969 discloses in most pertinent part a series of compounds having the formula

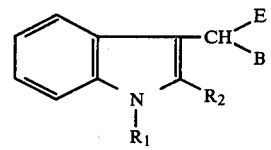

wherein inter alia $R_1$ and $R_2$ are independently hydrogen, alkyl or aryl; B is a carbocyclic or heterocyclic ring system, and E is alkoxy. The compounds are stated to be useful as intermediates in the preparation of triphenylmethane dyes.

M. Scholtz, Chem. Ber. 46, 2138–2146 (1913) discloses a group of (phenyl, substituted-phenyl or furyl)-(ethoxy or methoxy)(α-methylindolyl)methanes prepared by reacting an appropriate benzaldehyde or furfural with α-methylindole and ethanol or methanol in the presence of a base. No utility is disclosed for these compounds.

SUMMARY OF THE INVENTION

The present invention provides certain novel 1-$R_1$-2-$R_2$-3-[($R_3$O)(Z)methyl]-1H-indoles which are useful as color formers in pressure-sensitive carbonless duplicating systems and thermal marking systems. The compounds develop colored images of good tinctorial strength and have the advantage of good xerographic copiability and enhanced solubility in common organic solvents.

This invention also provides a novel process for preparing the above-described novel 1-$R_1$-2-$R_2$-3-[($R_3$O)(Z)methyl]-1H-indoles as well as certain known related compounds which comprises reacting a 1-$R_1$-2-$R_2$-3-[($R_3$-phenylsulfonyl)(Z)methyl]-1H-indole with an alcohol $R_3$OH in the presence of a base.

The invention further provides as an article of manufacture a pressure-sensitive carbonless duplicating system or thermal marking system which contains a support sheet coated with a color-forming substance comprising a novel 1-$R_1$-2-$R_2$-3-[($R_3$O)(Z)-methyl]-1H-indole

DETAILED DESCRIPTION OF THE INVENTION INCLUSIVE OF THE PREFERRED EMBODIMENTS

More specifically the invention sought to be patented resides in a composition of matter aspect in 1-$R_1$-2-$R_2$-3-[($R_3$O)(Z)methyl]-1H-indoles which are useful as color formers in pressure-sensitive duplicating systems and thermal marking systems and which have Formula I

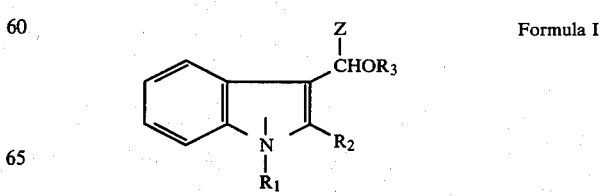

Formula I wherein:

$R_1$ is hydrogen or lower-alkyl;

$R_2$ is hydrogen, lower-alkyl or phenyl;

$R_3$ is alkyl containing 1 to 8 carbon atoms, di-lower-alkylamino-lower-alkyl, tri-lower-alkylammonium-lower-alkyl, benzyl or benzyl substituted in the phenyl ring with 1 or 2 lower-alkyl or lower-alkoxy groups, or a substituent having the formula

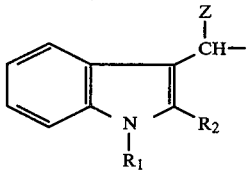

and

Z is biphenylyl, naphthyl or a substituent having the formula

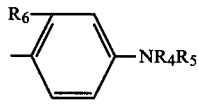

wherein $R_4$ and $R_5$ are independently lower-alkyl or benzyl, and $R_6$ is hydrogen, lower-alkyl, lower-alkoxy, halo or di-lower-alkylamino.

In another composition of matter aspect the invention sought to be patented resides in compounds of Formula I above useful as color formers in pressure-sensitive duplicating systems and thermal marking systems, wherein in said formula $R_1$ and $R_2$ have the previously given meanings;

$R_3$ is di-lower-alkylamino-lower-alkyl or tri-lower-alkylammonium-lower-alkyl, and Z is phenyl, tolyl or lower-alkoxy-phenyl.

A further composition of matter aspect of the invention sought to be patented resides in a compound, useful as a color former in pressure-sensitive duplicating systems and thermal marking systems, selected from the group consisting of 3-[(4-methoxyphenyl)(4-methoxybenzyloxy)methyl]-2-methyl-1H-indole;

3-[(4-methoxyphenyl)(benzyloxy)methyl]-2-methyl-1H-indole;

3-[3,4-dimethoxyphenyl)(methoxy)methyl]-2-methyl-1H-indole;

3-[(methoxy)(1-methyl-2-pyrrolyl)methyl]-1-ethyl-2-methyl-1H-indole;

3-[(9-ethyl-3-carbazolyl)(methoxy)methyl]-2-methyl-1H-indole; and

3-[(methoxy)(2-pyridyl)methyl]-2-methyl-1H-indole, or the group consisting of

3-[(methoxy(p-tolyl)methyl]-1H-indole;

3-[(methoxy)(4-methoxyphenyl)methyl]-1H-indole;

3-[(2-propoxy)(4-methoxyphenyl)methyl]-2-methyl-1H-indole;

3-[n-butoxy)(4-methoxyphenyl)methyl]-2-methyl-1H-indole;

3-[(methoxy)(2-methoxyphenyl)methyl]-2-methyl-1H-indole;

3-[(3,4-dichlorophenyl)(methoxy)methyl]-2-methyl-1H-indole;

3-[(2-furyl)(methoxy)methyl]-1-ethyl-2-methyl-1H-indole;

3-[(methoxy)(2-thienyl)methyl]-1H-indole;

3-[(methoxy)(2-thienyl)methyl]-2-methyl-1H-indole;

3-[(methoxy)(2-thienyl)methyl]-1-ethyl-2-methyl-1H-indole;

3-[(n-butoxy)(2-thienyl)methyl]-2-methyl-1H-indole; and

3-[(1-ethyl-2-methyl-1H-indol-3-yl)(methoxy)methyl]1-ethyl-2-methyl-1H-indole.

Preferred embodiments of this invention are compounds of Formula I hereinabove wherein $R_1$ and $R_2$ have the previously given meanings; $R_3$ is alkyl containing 1 to 8 carbon atoms or benzyl, and Z is a substituent having the formula

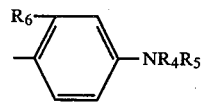

where $R_4$ and $R_5$ have the previously given meanings and $R_6$ is hydrogen. These compounds are especially valuable because they are obtained from inexpensive and readily available starting materials.

In an article of manufacture aspect the invention sought to be patented resides in a pressure-sensitive carbonless duplicating system or thermal marking system containing a support sheet coated with a color-forming substance comprising a compound having Formula I hereinabove wherein $R_1$ and $R_2$ have the previously given meanings;

$R_3$ is alkyl containing 1 to 8 carbon atoms, di-lower-alkylamino-lower-alkyl, tri-lower-alkylammonium-lower-alkyl, benzyl or benzyl-substituted in the phenyl ring with 1 or 2 lower-alkyl or lower-alkoxy groups, or a substituent having the formula

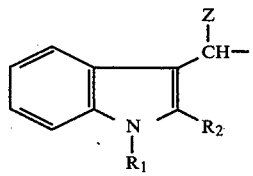

and

Z is biphenylyl, naphthyl or a substituent having the formula

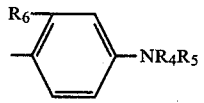

wherein $R_4$, $R_5$ and $R_6$ have the previously given definitions.

In another article of manufacture aspect the invention sought to be patented resides in a pressure-sensitive carbonless duplicating system or a thermal marking system containing a support sheet coated with a color-forming substance comprising a compound having Formula I hereinabove wherein:

$R_1$ and $R_2$ have the previously given meanings;

$R_3$ is di-lower-alkylamino-lower-alkyl or tri-lower-alkylammonium-lower-alkyl; and Z is phenyl, tolyl or lower-alkoxyphenyl.

In yet a further article of manufacture aspect the invention sought to be patented resides in a pressure-sensitive carbonless duplicating system or a thermal marking system containing a support sheet coated with a color-forming substance comprising a compound selected from the group consisting of 3-[(4-methoxyphenyl)(4-methoxybenzyloxy)methyl]-2-methyl-1H-indole;

3-[(4-methoxyphenyl)(benzyloxy)methyl]-2-methyl-1H-indole;

3-[(3,4-dimethoxyphenyl)(methoxy)methyl]-2-methyl-1H-indole;

3-[(methoxy)(1-methyl-2-pyrrolyl)methyl]-1-ethyl-2-methyl-1H-indole;

3-[(9-ethyl-3-carbazolyl)(methoxy)methyl]-2-methyl-1H-indole; and

3-[(methoxy)(2-pyridyl)methyl]-2-methyl-1H-indole, or the group consisting of

3-[(methoxy)(p-tolyl)methyl]-1H-indole;

3-[(methoxy)(4-methoxyphenyl)methyl]-1H-indole;

3-[(2-propoxy)(4-methoxyphenyl)methyl]-2-methyl-1H-indole;

3-[(n-butoxy)(4-methoxyphenyl)methyl]-2-methyl-1H-indole;

3-[(methoxy)(2-methoxyphenyl)methyl]-2-methyl-1H-indole;

3-[(3,4-dichlorophenyl)(methoxy)methyl]-2-methyl-1H-indole;

3-[(2-furyl)(methoxy)methyl]-1-ethyl-2-methyl-1H-indole;

3-[(methoxy)(2-thienyl)methyl]-1H-indole;

3-[(methoxy)(2-thienyl)methyl]-2-methyl-1H-indole;

3-[(methoxy)(2-thienyl)methyl]-1-ethyl-2-methyl-1H-indole;

3-[(n-butoxy)(2-thienyl)methyl]-2-methyl-1H-indole; and

3-[(1-ethyl-2-methyl-1H-indol-3-yl)(methoxy)methyl]-1-ethyl-2-methyl-1H-indole.

Preferred pressure-sensitive carbonless duplicating systems or thermal marking systems of the present invention are those which contain a color-forming substance comprising a compound of Formula I wherein $R_1$ and $R_2$ have the previously given meanings; $R_3$ is alkyl containing 1 to 8 carbon atoms or benzyl; and Z is a substituent having the formula

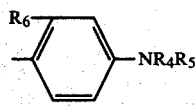

where $R_4$ and $R_5$ have the above-given meanings and $R_6$ is hydrogen.

In its process aspect the invention sought to be patented resides in a process for producing a compound having Formula I which comprises reacting a compound having Formula II

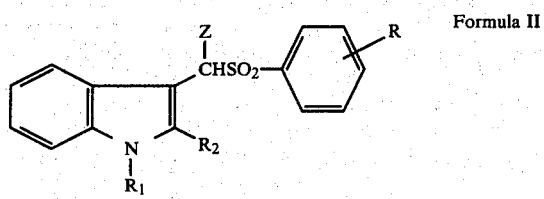

Formula II with an alcohol having Formula III $R_3OH$  Formula III in the presence of an alkali metal hydroxide or the alkali metal salt of the alcohol of Formula III wherein in said formulas R is hydrogen or lower-alkyl;

$R_1$ and $R_2$ have the previously given definitions;

$R_3$ is alkyl containing 1 to 8 carbon atoms; di-lower-alkylamino-lower-alkyl, tri-lower-alkylammonium-lower-alkyl, benzyl or benzyl substituted in the phenyl ring with 1 or 2 lower-alkyl or lower-alkoxy groups or a substituent having the formula

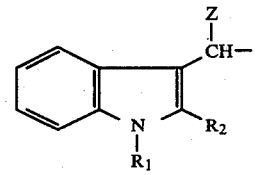

and

Z is lower-alkyl, biphenylyl, naphthyl, phenyl, phenyl substituted with 1 or 2 lower-alkyl, lower-alkoxy, halo or nitro groups, or a substituent having the formula

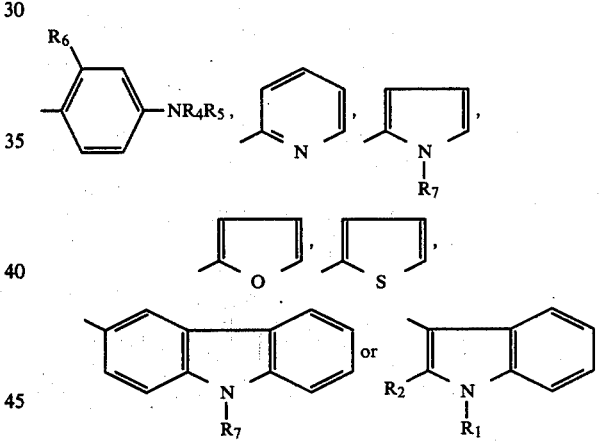

wherein $R_4$, $R_5$ and $R_6$ have the previously given meanings and $R_7$ is hydrogen or lower-alkyl.

As used herein the terms "lower-alkyl", "lower-alkoxy" and "di-lower-alkylamino-" denote saturated acyclic groups having from 1 to 4 carbon atoms which may be straight or branched as exemplified by methyl, ethyl, propyl, isopropyl, butyl, sec-butyl, isobutyl, t-butyl, methoxy, ethoxy, propoxy, isopropoxy, butoxy, sec-butoxy, isobutoxy, t-butoxy, dimethylamino, diethylamino, ethylmethylamino, dipropylamino, dibutylamino, isobutylmethylamino, t-butylmethylamino and the like.

The term "alkyl containing 1 to 8 carbon atoms" denotes saturated monovalent straight or branched chain aliphatic hydrocarbon radicals including methyl, ethyl, propyl, isopropyl, butyl, t-butyl, amyl, 1-methylbutyl, 3-methylbutyl, hexyl, isohexyl, heptyl, isoheptyl, octyl, isooctyl, 2-ethylhexyl and the like.

The term "tri-lower-alkyl-ammonium-lower-alkyl" signifies an amino-lower-alkyl radical in which the nitrogen atom is substituted by three sterically compatible lower-alkyl groups.

As used herein "tolyl" is intended to include ortho-, meta- and para-tolyl; "halo" includes chloro, fluoro, bromo and iodo and "alkali metal" includes lithium, sodium and potassium.

The novel compounds of Formula I hereinabove are essentially colorless in the depicted form. When contacted with an acidic medium, for example silica gel or one of the types ordinarily employed in pressure-sensitive carbonless duplicating systems such as silton clay or phenolic resin, the compounds of Formula I develop a yellow to deep purple image of good to excellent tinctorial strength and possess excellent xerographic copiability and enhanced solubility in common organic solvents. The compounds are thus highly suitable for use as colorless precursors, that is, color-forming substances in pressure-sensitive carbonless duplicating systems. Compounds producing darker purple colors can be used alone as color formers to produce images which are readily copiable whereas the compounds which produce a yellow to red color can be used as toners in admixture with other color formers to produce images of a neutral shade which desirably are readily copiable by xerographic means.

The compounds of this invention can be incorporated in any of the commercially accepted systems known in the carbonless duplicating art. A typical technique for such application is as follows: solutions containing one or more colorless precursor compounds of Formula I optionally in admixture with other color formers in suitable solvents are microencapsulated by well-known procedures, for example as described in U.S. Pat. Nos. 3,429,827, 3,649,649 and 4,000,087. The microcapsules are coated on the reverse side of a transfer sheet with the aid of a suitable binder. The coated transfer sheet is then assembled in a manifold with the microcapsule-coated side in contact with a receiving sheet coated with an electronic accepting substance, for example silton clay or phenolic resin. Application of pressure to the manifold such as that exerted by a stylus, typewriter or other form of writing or printing, causes the capsules on the reverse side to rupture. The solution of the color former released from the ruptured microcapsules flows to the receiving sheet and on contact with the acidic medium thereon forms a yellow to purple-colored image of good tinctorial strength. It is, of course, obvious that variants of this mode of application can be utilized, for example the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color-former.

It has also been found that when the compounds of Formula I are intimately mixed with an acidic developer of the type generally employed in thermal papers, for example bisphenol A as described in U.S. Pat. No. 3,539,375, that is, papers which produce a colored image when contacted with a heated stylus or heated type, heating of the mixture produces a colored image of varying shades from yellow to purple, depending on the particular compound of the invention employed. The ability of the compounds of Formula I to form a deep color when heated in admixture with an acidic developer such as bisphenol A makes them useful in thermal paper marking systems either where an original or a duplicate copy is prepared by contacting the thermal paper with a heated stylus or a heated type in any of the methods generally known in the art.

The compounds of this invention which are soluble in water or lower-alkanols, for example the compounds of Formula I wherein $R_3$ is tri-lower-alkylammonium-lower-alkyl can be incorporated in any of the commercial hectographic or spirit reproducing copying systems such as described in British Pat. No. 1,427,318, published Mar. 10, 1976. In such systems a transfer sheet coated on one side with a layer containing one or more water- or lower-alkanol-soluble color formers of Formula I is placed with its coated surface against one surface of a master paper which is then typed, written or marked on, causing transfer of the coating as a substantially colorless reverse image to the master paper at the points where the transfer sheet and master paper have been pressed together. The master paper is then brought into contact with a succession of sheets of paper moistened with a suitable spirit-reproducing fluid such as ethanol.

In accordance with the aforementioned process aspect of this invention, the above-described novel 1-$R_1$-2-$R_2$-3-[($R_3$O)(Z)methyl]-1H-indoles of Formula I as well as certain known related compounds are obtained by reacting a R-phenylsulfonyl compound of Formula II with an alcohol of Formula III in the presence of an alkali metal hydroxide or the alkali metal salt of said alcohol at a temperature of from about 0°–100° C. for approximately 10 minutes to 24 hours. The reaction is conveniently carried out in the presence of potassium hydroxide and at about 20°–60° C. for approximately 1 to 20 hours employing an excess of the alcohol as solvent. The product thus obtained can be isolated by filtration if it is insoluble in the reaction medium or by dilution of the reaction medium with a miscible solvent in which the produce is insoluble, such as water, a lower-alkanol, for example isopropyl alcohol, or a low molecular weight hydrocarbon, for example hexane, in order to effect precipitation of the product. Alternatively, the reaction mixture can be poured into water and the product extracted with an organic solvent such as benzene or toluene followed by evaporation of the organic solvent leading the product as a residue. The product, once isolated, can be purified by conventional means such as trituration or recrystallization from a suitable solvent.

The 3-[(R-phenylsulfonyl) (Z)methyl]-1H-indoles of Formula II which are required as starting materials in the above-described process are obtained by reacting approximately equimolar amounts of an appropriate 1-$R_1$-2-$R_2$-1H-indole, an appropriate aldehyde Z—CHO (Formula V) and an R-phenylsulfinic acid (R, $R_1$, $R_2$ and Z having the previously given meanings) in the presence of an acid catalyst such as hydrochloric acid, in a suitable solvent, for example N,N-dimethylformamide, or a lower-alkanol such as methanol, ethanol or 2-propanol at a temperature of about 5°–150° C. for approximately 1 to 35 hours. The reaction is usually carried out in ethanol at about 5°–60° C. for approximately 1 to 4 hours. The product thus obtained can be isolated by filtration if it is insoluble in the reaction medium or by the addition of a basic substance for example triethanolamine or ammonium hydroxide to effect precipitation of the product. Alternatively, the reaction mixture can be poured into water or a dilute aqueous base, for example ammonium hydroxide, sodium hydroxide, sodium carbonate or sodium bicarbonate and the product extracted with an organic solvent, such as benzene, chlorobenzene or toluene followed by evaporation of the organic solvent leaving the product as a residue. The product, once isolated, can be purified by conventional means such as trituration, recrystallization or slurrying in a suitable organic solvent.

The 1-$R_1$-2-$R_2$-1H-indoles as well as the aromatic or heterocyclic aldehydes of Formula V which are starting materials for preparing the 3-[(R-phenylsulfonyl) (Z)methyl]-1H-indoles of Formula II constitute well-known classes of compounds many of which are commercially available or readily obtained by conventional syntheses well known in the art.

The R-phenylsulfinic acids which are also required as starting materials for the intermediates of Formula II likewise belong to an old and well-known class of compounds. Sulfinic acids are known to be unstable and cannot be stored for long periods of time. Accordingly, in the above-described reaction the sulfinic acid is generated in situ by acidifying an alkali metal R-phenylsulfinate which in turn is readily obtained by conventional procedures, for example by reacting a R-phenylsulfonyl chloride with sodium sulfite and sodium bicarbonate in water. The sodium R-phenylsulfinate is stable and can be stored until needed. The R-phenylsulfonyl chlorides are, of course, readily available from the interaction of a R-phenylsulfonic acid or salt thereof with phosphorus oxychloride.

The compounds of Formula I hereinabove wherein $R_1$ is hydrogen, can also be prepared by reacting an indole of Formula IV containing an active hydrogen

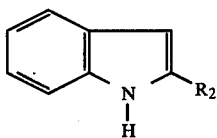

Formula IV with an aldehyde of Formula V

Z—CHO    Formula V and an alcohol of Formula III above ($R_2$ and Z having the previously given meanings) in an excess of the latter as solvent and in the presence of an alkali metal hydroxide or the alkali metal salt of the alcohol, at a temperature of from 0°–100° C. for approximately 0.5 hour to 5 days. Ordinarily, the reaction is carried out in the presence of potassium hydroxide at about 20°–30° C. for approximately 4 to 72 hours. The product so obtained can be isolated and purified as described hereinabove.

The molecular structures of the compounds of this invention were assigned on the basis of the modes of synthesis and study of their infrared and nuclear magnetic resonance spectra.

The following examples will further illustrate the invention without, however, limiting it thereto.

EXAMPLE 1

A. To a stirred mixture containing 175.0 ml. of ethyl alcohol, 27.5 ml. of concentrated hydrochloric acid, 30.4 g. of 86.4% sodium p-toluenesulfinate and 18.5 g. of p-(dimethylamino)benzaldehyde chilled to approximately 5° C. was slowly added 19.5 g. of 91.2% 1-ethyl-2-methyl-1H-indole. The resulting mixture was stirred approximately 3.5 hours at room temperature during which period the color changed from blue to yellow. The pH of the mixture was adjusted to approximately 8 by the addition of 40.0 g. of triethanolamine and after stirring approximately 20 minutes at room temperature the temperature was raised to and maintained at 55°–60° C. for approximately 20 minutes. After cooling to about 10° C. the resulting pink slid was collected by filtration and washed with 100 ml. of cold ethyl alcohol. The solid was then suspended in a mixture of 350 ml. of water and 10 g. of triethanolamine at room temperature for approximately 30 minutes, collected by filtration, washed successively with 150 ml. portions of 3% aqueous triethanolamine and water and dried under vacuum at 40° C. to give 42.2 g. of 3-{[4-(dimethylamino)-phenyl](4-methylphenylsulfonyl)methyl}-1-ethyl-2-methyl-1H-indole which softened at 155° C. and melted at 159°–161° C.

B. To a suspension of 4.5 g. of 3-{[4-(dimethylamino)-phenyl](4-methylphenylsulfonyl)methyl}-1-ethyl-2-methyl-1H-indole in 100 ml. of 2-propanol was added 1.5 g. of potassium hydroxide and the mixture stirred 1 hour at room temperature. The resulting solid was collected by filtration, washed successively with 2-propanol, water and 2-propanol, and dried to give 2.6 g. of 3-{[4-(dimethylamino)phenyl](2-propoxy)methyl}-1-ethyl-2-methyl-1H-indole which softened at 160° C., partially melted at 170°–172° C. and melted completely at 179°–187° C. A toluene solution of this product when contacted with acidic clay developed a bluish-red image and when contacted with phenolic resin developed a purple image.

EXAMPLE 2

Following a procedure similar to that described in Example 1B but employing 4.5 g. of 3{[4-(dimethylamino)phenyl](4-methylphenylsulfonyl)methyl}-1-ethyl-2-methyl-1H-indole, 30 ml. of 2-butanol and 1.5 g. of potassium hydroxide, there was obtained 2.6 g. of 3-{[4-(dimethylamino)phenyl](2-butoxy)methyl}-1-ethyl-2-methyl-1H-indole which softened at 140° C., partially melted at 159° C. and melted completely at 172°–174° C. A toluene solution of this product when contacted with acidic clay developed a red image and when contacted with phenolic resin developed a purple image.

EXAMPLE 3

A. To a stirred mixture containing 5.0 ml. of concentrated hydrochloric acid, 35 ml. of ethyl alcohol, 9.6 g. of 55.6% sodium p-toluenesulfinate and 2.9 g. of 1,2-dimethyl-1H-indole was added 3.8 g. of p-(dimethylamino)benzaldehyde. After stirring approximately 1 hour at 55°–60° C. the reaction mixture was cooled to about 40° C. and then diluted with 25 ml. of ethyl alcohol followed by 300 ml. of water and 200 g. of ice. The resulting solid was collected by filtration and washed with water. The product was suspended in 60 ml. of cold 2-propanol containing sufficient ammonium hydroxide to maintain a slightly alkaline condition and the resulting suspension stirred for approximately 45 minutes at 5°–10° C. The solid was then collected by filtration, washed with 15 ml. of fresh 2-propanol and dried under vacuum at 45° C. to afford 8.9 g. of 3-{[4-(dimethylamino)phenyl](4-methylphenylsulfonyl)methyl}-1,2-dimethyl-1H-indole, m.p. 179°–181° C.

B. Following a procedure similar to that described in Example 1B but employing 3.0 g. of 3-{[4-(dimethylamino)phenyl]-(4-methylphenylsulfonyl)methyl}-1,2-dimethyl-1H-indole, 30 ml. of 2-propanol and 1.0 g.

of potassium hydroxide there was obtained 1.9 g. of 3{[4-(dimethylamino)phenyl](2-propoxy)methyl}-1,2-dimethyl-1H-indole which softened at 178° C. and melted at 190°-195° C. A toluene solution of this product when contracted with acidic clay developed a red image and when contacted with phenolic resin developed a violet image.

EXAMPLE 4

A. Following a procedure similar to that described in Example 3A but employing 6.2 g. of 85.9% sodium p-toluenesulfinate, 4.5 g. of 94.4% 1-ethyl-2-methyl-1H-indole and 2.8 g. of thiophene-2-carboxaldehyde, there was obtained 10.0 g. of 3[(4-methylphenylsulfonyl)(2-thienyl)methyl]-1-ethyl-2-methyl-1H-indole, m.p. 168°-169° C. (dec.)

B. Following a procedure similar to that described in Example 1B but employing 5.0 g. of 3-[(4-methylphenylsulfonyl)(2-thienyl)methyl]-1-ethyl-2-methyl-1H-indole, 30 ml. of methanol and 2.0 g. of potassium hydroxide and stirring the reaction mixture 20 hours, there was obtained 2.6 g. of 3-[(methoxy)(2-thienyl)methyl]-1-ethyl-2-methyl-1H-indole which softened at 86° C. and melted at 89°-90° C. A toluene solution of this product when contacted with acidic clay or phenolic resin developed a yellow image.

EXAMPLE 5

A. Following a procedure similar to that described in Example 1A but employing 6.3 g. of 85% sodium p-toluenesulfinate, 2.2 g. of 98% 1-methylpyrrole-2-carboxaldehyde and 3.8 g. of 94% 1-ethyl-2-methyl-1H-indole, there was obtained 8.4 g. of 3-[(1-methyl-2-pyrrolyl)(4-methylphenylsulfonyl)methyl]-1-ethyl-2-methyl-1H-indole, m.p. 180° C.

B. Following a procedure similar to that described in Example 1B but employing 3.0 g. of 3-[(1-methyl-2-pyrrolyl)(4-methylphenylsulfonyl)methyl]-1-ethyl-2-methyl-1H-indole, 30 ml. of methanol and 1.0 g. of potassium hydroxide, there was obtained 1.7 g. of 3-[(methoxy)(1-methyl-2-pyrrolyl)methyl]-1-ethyl-2-methyl-1H-indole which softened at 125° C. and melted at 127°-129° C. A toluene solution of this product when contacted with acidic clay or phenolic resin developed an orange image.

EXAMPLE 6

A. Following a procedure similar to that described in 3A but employing 6.5 g. of 85.9% sodium p-toluenesulfinate, 4.6 g. of 1-ethyl-2-methyl-1H-indole-3-carboxaldehyde and 3.8 g. of 1-ethyl-2-methyl-1H-indole there was obtained 4.5 g. of 3-[(1-ethyl-2-methyl-1H-indol-3-yl)(4-methylphenylsulfonyl)methyl]-1-ethyl-2-methyl-1H-indole, m.p. 146°-152° C.

B. Following a procedure similar to that described in Example 1B but employing 5.0 g. of 3-[(1-ethyl-2-methyl-1H-indol-3-yl)(4-methylphenylsulfonyl)methyl-1H-indole, 50 ml. of methanol and 2 g. of potassium hydroxide there was obtained 2.2 g. of 3-[(1-ethyl-2-methyl-1H-indol-3-yl)(methoxy)methyl]-1-ethyl-2-methyl-1H-indole which softened at 94° C. and melted at 98°-108° C. A toluene solution of this product when contacted with acidic clay or phenolic resin developed an orange image.

EXAMPLE 7

To a mixture containing 5.0 g. of 3-{[4-(dimethylamino)phenyl](4-methylphenylsulfonyl)methyl}-1-ethyl-2-methyl1H-indole and 35 ml. of t-butanol was added 1.5 g. of potassium hydroxide and the resulting mixture heated 3 hours at 45° C. and then 4 hours at 60° C. The reaction mixture was diluted with 30 ml. of water and the resulting solid collected by filtration; washed successively with water, hexane and 2-propanol and dried to give 2.6 g. of pale yellow solid. Recrystallization from acetone-ethanol afforded 1.1 g. of bis-{[4-(dimethylamino)phenyl]-(1-ethyl-2-methyl-1H-indol-3-yl)methyl}ether which softened at 198° C., partially melted at 222°-225° C. and melted completely at 275° C. A toluene solution of this product when contacted with acidic clay developed a bluish-red image and when contacted with phenolic resin developed a purple image.

EXAMPLE 8

A. Following a procedure similar to that described in Example 3A but employing 6.5 g. of 81.9% sodium p-toluenesulfinate, 5.1 g. of 95% 2-phenyl-1H-indole and 3.8 g. of p-(dimethylamino)benzaldehyde, there was obtained 10.3 g. of 3-{[4-(dimethylamino)phenyl](4-methylphenylsulfonyl)methyl}-2-phenyl-1H-indole, m.p. 185.5°-188° C.

B. To a mixture containing 3.0 g. of 3-{[4-(dimethylamino)phenyl](4-methylphenylsulfonyl)methyl}-2-phenyl-1H-indole and 100 ml. of methanol was added 1.0 g. of potassium hydroxide. After stirring 3 hours at room temperature the reaction mixture was filtered to remove a small amount of insoluble material and the filtrate was poured into 500 ml. of water. The resulting precipitate was collected, washed with water and dried to give 2.2 g. of 3-{[4-(dimethylamino)phenyl](methoxy)methyl}-2-phenyl-1H-indole, m.p. 80°-118° C. A toluene solution of this product when contacted with acidic clay developed a violet image and when contacted with phenolic resin developed a chocolate brown image.

EXAMPLE 9

To a mixture containing 4.5 g. of 3-{[4-(dimethylamino)phenyl](4-methylphenylsulfonyl)methyl}-1-ethyl-2-methyl-1H-indole and 30 ml. of n-butanol was added 1.5 g. of potassium hydroxide. After stirring two hours at room temperature, the reaction mixture was poured into 1 liter of water and the product extracted with toluene. The toluene solution was washed with water and saturated aqueous sodium chloride and then evaporated to dryness under vacuum to give 3 g. of 3-{[(n-butoxy)[4-(dimethylamino)phenyl]methyl}-1-ethyl-2-methyl-1H-indole as a light tan oil. A toluene solution of this product when contacted with acidic clay developed a bluish-red image and when contacted with phenolic resin developed a violet image.

EXAMPLE 10

A. Following a procedure similar to that described in Example 3A but employing 6.5 g. of 81.9% sodium p-toluenesulfinate, 6.3 g. of 95% 4-(benzylethylamino)-benzaldehyde and 3.8 g. of 86.1% 1-ethyl-2-methyl-1H-indole, there was obtained 15.3 g. of 3-{[4-(benzylethylamino)phenyl](4-methylphenylsulfonyl)methyl}-1-ethyl-2-methyl-1H-indole as a gray tar-like product.

B. Following a procedure similar to that described in Example 9 but employing 4.0 g. of 3{[4-(benzylethylamino)phenyl](4-methylphenylsulfonyl)methyl}-1-ethyl-2-methyl-1H-indole, 100 ml. of methanol and 1 g. of potassium hydroxide and stirring the reaction mixture 3 hours there was obtained 2.6 g. of 3-{[4-(benzylethylamino)phenyl](methoxy)methyl}-1-ethyl-2-methyl-1H-indole as a brown oil. A toluene solution of this product when contacted with acidic clay developed a bluish-red image and when contacted with phenolic resin developed a purple image.

EXAMPLE 11

A. Following a procedure similar to that described in Example 3A but employing 6.5 g. of 81.9% sodium p-toluenesulfinate, 2.4 g. of furfural and 3.8 g. of 86.1% of 1-ethyl-2-methyl-1H-indole there was obtained 4.5 g. of 3-[(2-furyl)(4-methylphenylsulfonyl)methyl]-1-ethyl-2-methyl-1H-indole, m.p. 144°–146° C.

B. Following a procedure similar to that described in Example 9 but employing 5.0 g. of 3-[(2-furyl)(4-methylphenylsulfonyl)methyl]-1-ethyl-2-methyl-1H-indole, 75 ml. of methanol and 2.0 g. of potassium hydroxide and stirring the reaction mixture 4 hours, there was obtained following trituration of the product with hexane and 2-propanol approximately 0.1 g. of 3-[(2-furyl)(methoxy)methyl]-1-ethyl-2-methyl-1H-indole as a tan solid, m.p. 165° C. (dec.). A toluene solution of this product when contacted with acidic clay or phenolic resin developed a yellow image.

EXAMPLE 12

Following a procedure similar to that described in Example 9 but employing 8.92 g. of 3-{[4-(dimethylamino)phenyl]-(4-methylphenylsulfonyl)methyl}-1-ethyl-2-methyl-1H-indole, 80 ml. of methanol and 3.0 g. of potassium hydroxide and heating the reaction mixture at 45° C. for 20 hours, there was obtained following trituration of the product with hexane 4.28 g. of 3-{[4-(dimethylamino)phenyl](methoxy)methyl}-1-ethyl-2-methyl-1H-indole as a pale pink solid, m.p. 76°–83° C. A toluene solution of this product when contacted with acidic clay or phenolic resin developed a bluish-red image.

EXAMPLE 13

Following a procedure similar to that described in Example 9 but employing 3.0 g. of 3-{[4-(dimethylamino)phenyl]-(4-methylphenylsulfonyl)methyl}-1,2-dimethyl-1H-indole, 30 ml. of n-hexanol and 1.0 g. of potassium hydroxide, stirring the reaction mixture 18 hours and removing excess n-hexanol by vacuum distillation (temperature maintained below 50° C.), there was obtained 2.3 g. of 3-{[4-(dimethylamino)phenyl](n-hexyloxy)methyl}-1,2-dimethyl-1H-indole. A sample crystallized from hexane softened at 125° C. and melted at 168°–206° C. A toluene solution of this product when contacted with acidic clay or phenolic resin developed a bluish-red image.

EXAMPLE 14

To a mixture containing 6.8 g. of 3-{[4-(dimethylamino)phenyl](4-methylphenylsulfonyl)methyl}-1-ethyl-2-methyl-1H-indole and 35 ml. of benzyl alcohol was added 2.0 g. of potassium hydroxide. After stirring 2 hours at room temperature the reaction mixture was poured into water and the product extracted with toluene. The toluene extracts were steam distilled to remove excess benzyl alcohol. The gummy residue was dissolved in 200 ml. of acetone and the resulting solution added slowly to 1 liter of 1% aqueous ammonia. The resulting solid was collected, washed with water and dried to give 3.4 g. of 3-{(benzyloxy)[4-(dimethylamino)phenyl]methyl}-1-ethyl-2-methyl-1H-indole, m.p. 53°–77° C. A toluene solution of this product when contacted with acidic clay developed a red image and when contacted with phenolic resin developed a violet image.

EXAMPLE 15

A mixture containing 6.5 g. of 2-methyl-1H-indole, 6.0 g. of p-tolylaldehyde and 3.0 g. of potassium hydroxide in 50 ml. of methanol was stirred 44 hours at room temperature. The solid which formed was collected by filtration and washed with 2-propanol. The product was then slurried in 300 ml. of 50% aqueous methanol, filtered and washed with methanol to give 6.4 g. of 3-[(methoxy)(p-tolyl)methyl]-2-methyl-1H-indole, m.p. 156°–159° C. A toluene solution of this product when contacted with acidic clay or phenolic resin developed a yellow image.

EXAMPLE 16

Following a procedure similar to that described in Example 15 but employing 5.9 g. of indole, 6.0 g. of p-tolylaldehyde, 40 ml. of methanol and 3.0 g. of potassium hydroxide and stirring the reaction mixture 1 day, there was obtained 4.51 g. of 3-[(methoxy)(p-tolyl)methyl]-1H-indole, m.p. 96°–98° C. A toluene solution of this product when contacted with acidic clay or phenolic resin developed a yellow image.

EXAMPLE 17

Following a procedure similar to that described in Example 15 but employing 6.5 g. of 2-methyl-1H-indole, 5.6 g. of 2-thiophenecarboxyaldehyde, 50 ml. of methanol and 3.0 g. of potassium hydroxide and stirring the reaction mixture 24 hours, there was obtained 9.45 g. of 3-[(methoxy)(2-thienyl)methyl]-2-methyl-1H-indole, m.p. 116°–122° C. A toluene solution of this product when contacted with acidic clay or phenolic resin developed a yellow image.

EXAMPLE 18

Following a procedure similar to that described in Example 15 but employing 6.0 g. of indole, 5.8 g. of 2-thiophenecarboxaldehyde, 50 ml. of methanol and 3.0 g. of potassium hydroxide and stirring the reaction mixture 4 hours, there was obtained 2.6 g. of 3-[(methoxy)(2-thienyl)methyl]-1H-indole, m.p. 107°–112° C. A toluene solution of this product when contacted with acidic clay developed a pinkish-yellow image and when contacted with phenolic resin developed a yellow image.

EXAMPLE 19

Following a procedure similar to that described in Example 15 but employing 6.5 g. of 2-methyl-1H-indole, 9.2 g. of 4-phenylbenzaldehyde, 100 ml. of methanol and 3.0 g. of potassium hydroxide and stirring the reaction mixture 2 days, there was obtained 4.6 g. of 3-[(4-biphenylyl)(methoxy)methyl]-2-methyl-1H-indole, m.p. 170°–173° C. A toluene solution of this product when contacted with acidic clay developed a yellow image.

EXAMPLE 20

Following a procedure similar to that described in Example 15 but employing 6.5 g. of 2-methyl-1H-indole, 6.8 g. of p-anisaldehyde, 60 ml. of methanol and 3.0 g. of potassium hydroxide and stirring the reaction mixture 66 hours, there was obtained 12.0 g. of 3-[(4-methoxyphenyl)(methoxy)methyl]-2-methyl-1H-indole, m.p. 150.5°–153.8° C. A toluene solution of this product when contacted with acidic clay developed an orange-yellow image.

EXAMPLE 21

Following a procedure similar to that described in Example 15 but employing 6.5 g. of 2-methyl-1H-indole, 8.3 g. of 3,4-dimethoxybenzaldehyde, 50 ml. of methanol and 3.0 g. of potassium hydroxide and stirring the reaction mixture 20 hours, there was obtained 7.1 g. of 3-[(3,4-dimethoxyphenyl)(methoxy)methyl]-2-methyl-1H-indole, m.p. 148°–149° C. A toluene solution of the product when contacted with acidic clay or phenolic resin developed an orange-yellow image.

EXAMPLE 22

Following a procedure similar to that described in Example 15 but employing 6.5 g. of 2-methyl-1H-indole, 7.2 g. of p-chlorobenzaldehyde, 50 ml. of methanol and 3.0 g. of potassium hydroxide and stirring the reaction mixture 1 day, there was obtained 1.1 g. of 3-[(4-chlorophenyl)(methoxy)methyl]-2-methyl-1H-indole, m.p. 98°–99.5° C. A toluene solution of this product when contacted with acidic clay developed a yellow image.

EXAMPLE 23

Following a procedure similar to that described in Example 15 but employing 6.5 g. of 2-methyl-1 H-indole, 5.3 g. of benzaldehyde, 25 ml. of methanol and 3.0 g. of potassium hydroxide, and stirring the reaction mixture 7 hours, there was obtained 7.56 g. of 3-[(phenyl)(methoxy)methyl]-2-methyl-1H-indole, m.p. 251°–253° C. A toluene solution of the product when contacted with acidic clay or phenolic resin developed an orange image.

EXAMPLE 24

A. Following a procedure similar to that described in Example 15 but employing 6.5 g. of 2-methyl-1H-indole, 5.3 g. of benzaldehyde, 25 ml. of 2-(dimethylamino)ethanol and 3.0 g. of potassium hydroxide and stirring the reaction mixture 41 hours, there was obtained 6.34 g. of 3-{[2-(dimethylamino)ethoxy](phenyl)methyl}-2-methyl-1H-indole, m.p. 134.5°–135° C. A toluene solution of this product when contacted with acidic clay developed a yellow image.

B. Stirring for 0.5 hour a mixture containing 1.0 g. of the product of part A above, 1 ml. of methyl iodide, 50 ml. of chlorobenzene and 50 ml. of toluene; collection of the solid produced; washing with toluene and drying, afforded 1.1 g. of the corresponding methiodide, m.p. 113°–130° C.

EXAMPLE 25

To a solution containing 3.2 g. of 2-methyl-1H-indole and 3.0 g. of 4-(dimethylamino)benzaldehyde in 50 ml. of methanol at 5° C. was added 1.5 g. of potassium hydroxide. The resulting mixture was then stirred 5 days at room temperature and the solid which precipitated was collected and washed with 2-propanol to give 1.4 g. of 3-{[4-(dimethylamino)phenyl](methoxy)methyl}-2-methyl-1-H-indole, m.p. 172°–177° C. A toluene solution of this product when contacted with acidic clay or phenolic resin developed a deep red image.

EXAMPLE 26

Following a procedure similar to that described in Example 25 but employing 6.5 g. of 2-methyl-1H-indole, 5.5 g. of 2-pyridinecarboxaldehyde, 50 ml. of methanol and 3.0 g. of potassium hydroxide, and stirring the reaction mixture 4 hours at room temperature there was obtained 10.6 g. of 3-[(methoxy)(2-pyridyl)methyl]-2-methyl-1H-indole, m.p. 174°–177° C. When contacted with silica gel, this product developed an orange-pink image.

EXAMPLE 27

Following a procedure similar to that described in Example 25, but employing 6.5 g. of 2-methyl-1H-indole, 5.0 g. of furfural, 50 ml. of methanol and 3.0 g. of potassium hydroxide, and stirring the reaction mixture 2 hours at room temperature there was obtained 5.0 g. of 3-[(2-furyl)(methoxy)methyl]-2-methyl-1H-indole, m.p. 119°–121° C. A toluene solution of this product when contacted with acidic clay or phenolic resin developed a yellow image.

EXAMPLE 28

A mixture containing 13.0 g. of 2-methyl-1H-indole, 17.5 g. of 3,4-dichlorobenzaldehyde, 100 ml. of methanol and 5 g. of potassium hydroxide was stirred 3 days at room temperature. The reaction mixture was diluted with 10 ml. of water and the resulting solid was collected by filtration, washed with 2-propanol and hexane and then dried. Recrystallization from 2-propanol-hexane afforded 7.7 g. of 3-[(3,4-dichlorophenyl)(methoxy)methyl]-2-methyl-1H-indole, m.p. 118°–119° C. A toluene solution of the product contacted with acidic clay or phenolic resin developed a greenish-yellow image.

EXAMPLE 29

To a solution containing 6.5 g. of 2-methyl-1H-indole, 7.6 g. of m-nitrobenzaldehyde, in 100 ml. of methanol was added 3.0 g. of potassium hydroxide. After stirring 3 days at room temperature the reaction mixture was poured into 400 ml. of water and the gummy material which separated was extracted with toluene. The toluene solution was washed with water and saturated sodium chloride solution and then evaporated to dryness under vacuum. The residue was triturated with 200 ml. of hexane followed by 100 ml. of 2-propanol to give 4.2 g. of 3-[(methoxy)(3-nitrophenyl)methyl]-2-methyl-1H-indole, m.p. 134°–143.5° C. A toluene solution of this product when contacted with acidic clay or phenolic resin developed a yellow image.

EXAMPLE 30

Following a procedure similar to that described in Example 29 but employing 5.9 g. of indole, 6.8 g. of p-anisaldehyde, 50 ml. of methanol and 3.0 g. of potassium hydroxide and stirring the reaction mixture for one day, there was obtained 11.4 g. of 3-[(methoxy)(4-methoxyphenyl)methyl]-1H-indole as a pale yellow oil. A toluene solution of this product when contacted with acidic clay developed an orange red image and when contacted with phenolic resin developed an orange-yellow image.

EXAMPLE 31

Following a procedure similar to that described in Example 29 but employing 6.5 g. of 2-methyl-1H- indole, 6.8 g. of o-anisaldehyde, 50 ml. of methanol and 3.0 g. of potassium hydroxide, and stirring the reaction mixture 2 days, there was obtained 3.4 g. of 3-[(methoxy)(2-methoxyphenyl)methyl]-2-methyl-1H-indole, m.p. 121°–128° C. A toluene solution of this product when contacted with acidic clay developed an orange-yellow image and when contacted with phenolic resin developed a yellow image.

EXAMPLE 32

Following a procedure similar to that described in Example 29 but employing 3.3 g. of 2-methyl-1H-indole, 5.6 g. of 9-ethyl-3-carbazolecarboxaldehyde, 50 ml. of methanol and 2 g. of potassium hydroxide and stirring the reaction mixture 3 days, there was obtained 6.2 g. of 3-[(9-ethylcarbazol-3-yl)(methoxy)methyl]-2-methyl-1H-indole as a brown gummy material. A toluene solution of this product when contacted with acidic clay or phenolic resin developed a pink-red image.

EXAMPLE 33

A. Following a procedure similar to that described in Example 29 but employing 6.5 g. of 2-methyl-1H-indole, 6.5 g. of p-anisaldehyde, 20 ml. of 2-(dimethylamino)ethanol and 3.0 g. of potassium hydroxide and stirring the reaction mixture 1 day, there was obtained 6.4 g. of 3-{[2-(dimethylamino)ethoxy](4-methoxyphenyl)methyl}-2-methyl-1H-indole, m.p. 84°–88° C. A toluene solution of this product when contacted with acidic clay or phenolic resin developed a yellow image.

B. Stirring for 0.5 hour a mixture containing 1.5 g. of the product of part A above, 1 ml. of methyl iodide and 30 ml. of toluene; collecting the solid produced and washing with toluene afforded 0.95 g. of the corresponding methiodide, m.p. 144°–151° C.

EXAMPLE 34

A mixture containing 6.5 g. of 2-methyl-1H-indole, 6.5 g. of p-anisaldehyde, 20 g. of 4-methoxybenzyl alcohol and 3.0 g. of potassium hydroxide was stirred 24 hours at room temperature. The reaction mixture was diluted with 50 ml. of hexane and 50 ml. of 2-propanol and the resulting solid was collected, washed with 2-propanol and dried to give 0.7 g. of 3-[(4-methoxybenzyloxy)(4-methoxyphenyl)methyl]-2-methyl-1H-indole, m.p. >300° C. A toluene solution of this product when contacted with acidic clay or phenolic resin developed a yellow image.

EXAMPLE 35

Following a procedure similar to that described in Example 34 but employing 6.5 g. of 2-methyl-1H-indole, 6.5 g. of p-anisaldehyde, 20 g. of n-butanol and 3.0 g. of potassium hydroxide, and stirring the reaction mixture 24 hours at room temperature there was obtained 12.4 g. of 3-[(n-butoxy)(4-methoxyphenyl)methyl]-2-methyl-1H-indole, m.p. 89°–91° C. A toluene solution of this product when contacted with acidic clay or phenolic resin developed a yellow image.

EXAMPLE 36

Following a procedure similar to that described in Example 34 but employing 6.5 g. of 2-methyl-1H-indole, 6.5 g. of p-anisaldehyde, 30 g. of benzyl alcohol and 3.0 g. of potassium hydroxide, and stirring the reaction mixture 2 days at room temperature there was obtained 12.9 g. of 3-[(benzyloxy)(4-methoxyphenyl)methyl]-2-methyl-1H-indole, m.p. 118°–121° C. A toluene solution of this product when contacted with acidic clay or phenolic resin developed a yellow image.

EXAMPLE 37

Following a procedure similar to that described in Example 34 but employing 6.5 g. of 2-methyl-1H-indole, 5.6 g. of 2-thiophenecarboxaldehyde, 20 ml. of benzyl alcohol and 3.0 g. of potassium hydroxide, and stirring the reaction mixture 40 hours at room temperature, there was obtained 3.21 g. of 3-[(benzyloxy)(2-thienyl)methyl]-2-methyl-1H-indole, m.p. 22 300° C. A toluene solution of this product when contacted with acidic clay or phenolic resin developed a yellow image.

EXAMPLE 38

Following a procedure similar to that described in Example 34 but employing 6.5 g. of 2-methyl-1H-indole, 15.6 g. of 2-thiophenecarboxaldehyde, 20 ml. of n-butanol and 3.0 g. of potassium hydroxide and stirring the reaction mixture 16 hours at room temperature there was obtained 5.76 g. of 3-[(n-butoxy)(2-thienyl)methyl]-2-methyl-1H-indole, m.p. 253.5°–255° C. A toluene solution of this product when contacted with acidic clay or phenolic resin developed a yellow image.

EXAMPLE 39

A mixture containing 6.5 g. of 2-methyl-1H-indole, 7.8 g. of 1-naphthaldehyde, 35 ml. of methanol and 3.0 g. of potassium hydroxide was stirred 4 days at room temperature. The reaction mixture was poured into 400 ml. of water and the aqueous solution was decanted from the resulting gummy precipitate. The latter was washed with hexane and then evaporated to dryness under vacuum to afford 10.2 g. of 3-[(methoxy)(1-naphthyl)methyl]-2-methyl-1H-indole, as a brown oil. A toluene solution of this product when contacted with acidic clay or phenolic resin developed a yellow image.

EXAMPLE 40

A mixture containing 6.5 g. of 2-methyl-1H-indole, 6.8 g. of p-anisaldehyde, 60 ml. of 2-propanol and 3.0 g. of potassium hydroxide was stirred 3 days at room temperature. The product which separated from the reaction mixture as a gum was crystallized from 2-propanol to give a first crop of 1.3 g. of yellow solid, m.p. 153.5°–160° C. A toluene solution of this product when contacted with acidic clay developed a yellow image. Dilution of the filtrate with water afforded a second crop, m.p. 148°–151° C. and a third crop, m.p. 125°–130° C. Nuclear magnetic resonance spectral analysis of the first and third crops indicated each to be a mixture of 3-[(4-methoxyphenyl)(2-propoxy)methyl]-2-methyl-1H-indole (I) and 3-[(4-methoxyphenyl)(2-methyl-1H-indol-3-yl)methyl]-2-methyl-1H-indole (II). The first crop contained 16% I and 84% II and the third crop contained 35% I and 65% II.

It is contemplated that by following procedures similar to those described in the foregoing examples but employing the appropriate 1-$R_1$-2-$R_2$-3-[(R-phenylsulfonyl)(Z)methyl]-1H-indole and the appropriate alcohol $R_3OH$ there will be obtained the 1-$R_1$-2-$R_2$-3-[($R_3O$)(Z)methyl]-1H-indoles of Formula I, Examples 41–50 presented in Table A hereinbelow.

TABLE A

1-R$_1$—2-R$_2$—3-[(R$_3$O)(Z)methyl]-1H-indoles of Formula I

| Ex. | R$_1$ | R$_2$ | R$_3$ | Z |
|---|---|---|---|---|
| 41 | C$_2$H$_5$ | CH$_3$ | C$_8$H$_{17}$ | 4-(CH$_3$)$_2$N—C$_6$H$_4$ |
| 42 | n-C$_4$H$_9$ | H | CH$_3$ | 4-(n-C$_4$H$_9$)$_2$N—C$_6$H$_3$ |
| 43 | C$_2$H$_5$ | CH$_3$ | CH$_3$ | 2-Cl—4-(CH$_3$)$_2$N—C$_6$H$_3$ |
| 44 | C$_2$H$_5$ | CH$_3$ | CH$_3$ | 2,4-[(CH$_3$)$_2$N]$_2$—C$_6$H$_3$ |
| 45 | CH$_3$ | CH$_3$ | 4-CH$_3$—C$_6$H$_4$ | 2-C$_2$H$_5$O—4-(C$_2$H$_5$)$_2$N—C$_6$H$_3$ |
| 46 | H | CH$_3$ | C$_2$H$_5$ | 2-CH$_3$—4-(CH$_3$)$_2$N—C$_6$H$_3$ |
| 47 | H | H | 3,4-(CH$_3$O)$_2$—C$_6$H$_3$CH$_2$ | 4-(CH$_3$)$_2$N—C$_6$H$_4$ |
| 48 | C$_2$H$_5$ | CH$_3$ | 4-(C$_2$H$_5$)$_2$N—(CH$_2$)$_4$— | 4-(CH$_3$)$_2$N—C$_6$H$_4$ |
| 49 | CH$_3$ | CH$_3$ | CH$_3$ | 2-naphthyl |
| 50 | CH$_3$ | C$_5$H$_5$ | CH$_3$ | 2-F—4-(CH$_3$)$_2$N—C$_6$H$_3$ |

EXAMPLE 51

The color former of Example 20 was microencapsulated and applied to a carbonless duplicating transfer sheet as follows: a solution prepared by dissolving 0.73 g. of the color former in 30 g. of isopropylbiphenyl at 95° C. and a solution prepared by slowly dissolving 2.5 g. of carboxymethylcellulose in 100 ml. of distilled water were mixed and emulsified by rapid stirring at 50° C. The desired particle size (1-2 microns) was checked by microscope. A solution prepared by dissolving 7.5 g. of pigskin gelatin in 60 ml. of distilled water at 50° C. followed by stirring approximately one hour at 50° C. was then added to the stirred emulsion and the pH was adjusted to 6.5 with 10% aqueous sodium hydroxide with rapid stirring. Following the gradual addition of 335 ml. of distilled water at 50° C. the pH was adjusted to 4.5 with 10% aqueous acetic acid with continued rapid stirring. After five minutes the mixture was cooled to 15° C. and 5 ml. of 25% aqueous glutaraldehyde was added dropwise while rapid stirring was continued an additional 15 minutes. After stirring more slowly overnight the weight of the microcapsule dispersion was adjusted to 560 g. with distilled water to give a color former concentration of approximately 0.13%. White typewriter paper sheets (transfer sheets) were coated with this dispersion at a film thickness of 0.0015 inch and air-dried. The coated side of a transfer sheet was placed in contact with a receiving sheet coated with either phenolic resin or acidic clay. Typing on the transfer sheet produced a yellow duplicate typewritten image on the receiving sheet.

EXAMPLE 52

The color former of Example 12 was microencapsulated and applied to a carbonless duplicating transfer sheet as follows: A solution prepared by dissolving 1.46 g. of the color former in 60 g. of dibutyl phthalate at 100° C. then cooling to 50° C. and a solution prepared by slowly dissolving 5 g. of carboxymethylcellulose in 200 ml. of distilled water were mixed and emulsified by rapid stirring. The desired particle size (5 microns) was checked by microscope. A solution prepared by dissolving 15 g. of pigskin gelatin in 120 ml. of distilled water at 50° C. followed by stirring 1 hour at 50° C. was then added to the stirred emulsion and the pH was adjusted to 6.5 with 10% aqueous sodium hydroxide with rapid stirring. Following the gradual addition of 670 ml. of water at 50° C. the pH was adjusted to 4.5 with 10% aqueous acetic acid with continued rapid stirring. After 5 minutes the mixture was cooled to 15° C. and 10 ml. of 25% aqueous glutaraldehyde was added dropwise while rapid stirring was continued an additional 15 minutes. After stirring more slowly overnight, the weight of the microcapsule dispersion was adjusted to 1120 g. with distilled water to give a color former concentration of approximately 0.13%. White typewriter paper sheets (transfer sheets) were coated with this dispersion at a film thickness of 0.0015 inches and air-dried. The coated side of a transfer sheet was placed in contact with a receiving sheet coated with either phenolic resin or acidic clay. Typing on the transfer sheet produced a violet duplicate type-written image on the receiving sheet.

EXAMPLE 53

The color formers of Examples 12 and 25 were incorporated in thermal papers essentially as described in U.S. Pat. No. 3,539,375. Polyvinyl alcohol dispersions of the color formers of Examples 12 and 25 were prepared by shaking 1 hour on a paint shaker a mixture containing 2.0 g. of the color former, 3.7 g. of water, 8.6 g. of 10% aqueous polyvinyl alcohol and 10 ml. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied at a thickness of 0.0015 inch to white paper sheets and the sheets were dried at room temperature. Contacting the coated sheets with a heated stylus at temperatures between 100° C. and 160° C. produced a violet to purple image on the sheet coated with the color former of Example 12 and a red-violet to blue-violet image on the sheet coated with the color former of Example 25.

We claim:

1. A pressure-sensitive carbonless duplicating system or thermal marking system containing a support sheet coated with a color-forming substance comprising a compound having the formula

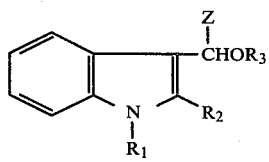

wherein:
R$_1$ is hydrogen or lower-alkyl;
R$_2$ is hydrogen, lower-alkyl or phenyl;
R$_3$ is alkyl containing 1 to 8 carbon atoms, dilower-alkylamino-lower-alkyl, tri-lower-alkylammonium-lower-alkyl, benzyl or benzyl substituted in the phenyl ring with 1 or 2 lower-alkyl or lower-alkoxy groups, or $R_3$ is a substituent having the formula

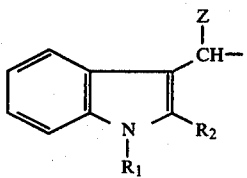

and

Z is biphenylyl, naphthyl or a substituent having the formula

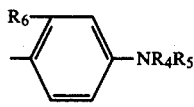

wherein $R_4$ and $R_5$ are independently lower-alkyl or benzyl, and $R_6$ is hydrogen, lower-alkyl, lower-alkoxy, halo or di-lower-alkylamino.

2. A pressure-sensitive carbonless duplicating system or thermal marking system according to claim 1 wherein:

$R_3$ is lower-alkyl, and

Z is a substituent having the formula

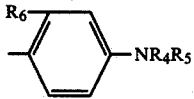

where $R_4$ and $R_5$ are each lower-alkyl and $R_6$ is hydrogen.

3. A pressure-sensitive carbonless duplicating system or thermal marking system containing a support sheet coated with a color-forming substance comprising a compound having the formula

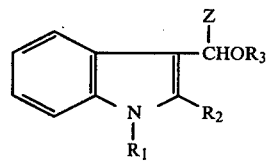

wherein:
$R_1$ is hydrogen or lower-alkyl;
$R_2$ is hydrogen, lower-alkyl or phenyl;
$R_3$ is di-lower-alkylamino-lower-alkyl or tri-lower-alkylammonium-lower-alkyl; and
Z is phenyl, tolyl or lower-alkoxyphenyl.

4. A pressure-sensitive carbonless duplicating system or thermal marking system containing a support sheet coated with a color-forming substance comprising a compound selected from the group consisting of
  3-[(4-methoxyphenyl)(4-methoxybenzyloxy)methyl]-2-methyl-1H-indole;
  3-[(4-methoxyphenyl)(benzyloxy)methyl]-2-methyl-1H-indole;
  3-[(3,4-dimethoxyphenyl)(methoxy)methyl]-2-methyl-1H-indole;
  3-[(methoxy)(1-methyl-2-pyrrolyl)methyl-1-ethyl-2-methyl-1H-indole;
  3-[(9-ethyl-3-carbazolyl)(methoxy)methyl]-2-methyl-1H-indole; and
  3-[(methoxy)(2-pyridyl)methyl]-2-methyl-1H-indole.

5. A pressure-sensitive carbonless duplicating system or thermal marking system containing a support sheet coated with a color-forming substance comprising a compound selected from the group consisting of:
  3-[(methoxy)(p-tolyl)methyl]-1H-indole;
  3-[(methoxy)(4-methoxyphenyl)methyl]-1H-indole;
  3-[(2-propoxy)(4-methoxyphenyl)methyl]-2-methyl-1H-indole;
  3-[(n-butoxy)(4-methoxyphenyl)methyl]-2-methyl-1H-indole;
  3-[(methoxy)(2-methoxyphenyl)methyl]-2-methyl-1H-indole;
  3-[(3,4-dichlorophenyl)(methoxy)methyl]-2-methyl-1H-indole;
  3-[(2-furyl)(methoxy)methyl]-1-ethyl-2-methyl-1H-indole;
  3-[(methoxy)(2-thienyl)methyl]-1H-indole;
  3-[(methoxy)(2-thienyl)methyl]-2-methyl-1H-indole;
  3-[(methoxy)(2-thienyl)methyl]-1-ethyl-2-methyl-1H-indole;
  3-[(n-butoxy)(2-thienyl)methyl]-2-methyl-1H-indole; and
  3-[(1-ethyl-2-methyl-1H-indole-3-yl)(methoxy)methyl]-1-ethyl-2-methyl-1H-indole.

* * * * *